United States Patent [19]

Wright

[11] 3,999,420
[45] Dec. 28, 1976

[54] LENS IMPACT HAMMER APPARATUS AND METHODS

[76] Inventor: John F. Wright, P.O. Box 4041, Richardson, Tex. 75080

[22] Filed: Feb. 26, 1975

[21] Appl. No.: 553,259

[52] U.S. Cl. .................................................. 73/12
[51] Int. Cl.$^2$ .......................................... G01N 3/14
[58] Field of Search ................................. 73/12, 82

[56] References Cited

UNITED STATES PATENTS

| | | | |
|---|---|---|---|
| 2,362,589 | 11/1944 | Simmons | 73/12 |
| 2,388,246 | 11/1945 | Berger | 73/12 |
| 2,396,620 | 3/1946 | Taxwood | 73/12 |
| 2,778,219 | 1/1957 | Wachter | 73/12 |
| 3,209,585 | 10/1965 | Wolstenholme et al. | 73/12 |
| 3,488,991 | 1/1970 | Dietert et al. | 73/12 |
| 3,724,260 | 4/1973 | Bole | 73/12 |

FOREIGN PATENTS OR APPLICATIONS

| | | | |
|---|---|---|---|
| 395,928 | 5/1923 | Germany | 73/82 |

Primary Examiner—James J. Gill
Assistant Examiner—Anthony V. Ciarlante
Attorney, Agent, or Firm—Hubbard, Thurman, Turner & Tucker

[57] ABSTRACT

Hammer apparatus is provided for impacting an eyeglass lens to test the frangibility of the lens. A hammer arm is pivotally mounted on a base plate for rotation between a vertical position and a horizontal position. A steel ball is connected to the end of the hammer arm to impact the lens. A weight is positioned precisely on the hammer arm to provide the exact amount of impact force required by FDA regulations. A cylindrical pedestal is mounted to the base plate to support the lens horizontally so that the ball strikes substantially in the center of the lens when the hammer arm falls to the horizontal position. A catch member holds the hammer arm in the vertical position and, upon manual actuation, the catch member releases the hammer arm to fall to impact the lens. A removable metal box encloses the pedestal for catching broken glass. The top of the box includes an aperture for the ball to enter as the arm falls to impact the lens.

18 Claims, 6 Drawing Figures

U.S. Patent   Dec. 28, 1976   Sheet 2 of 2   3,999,420
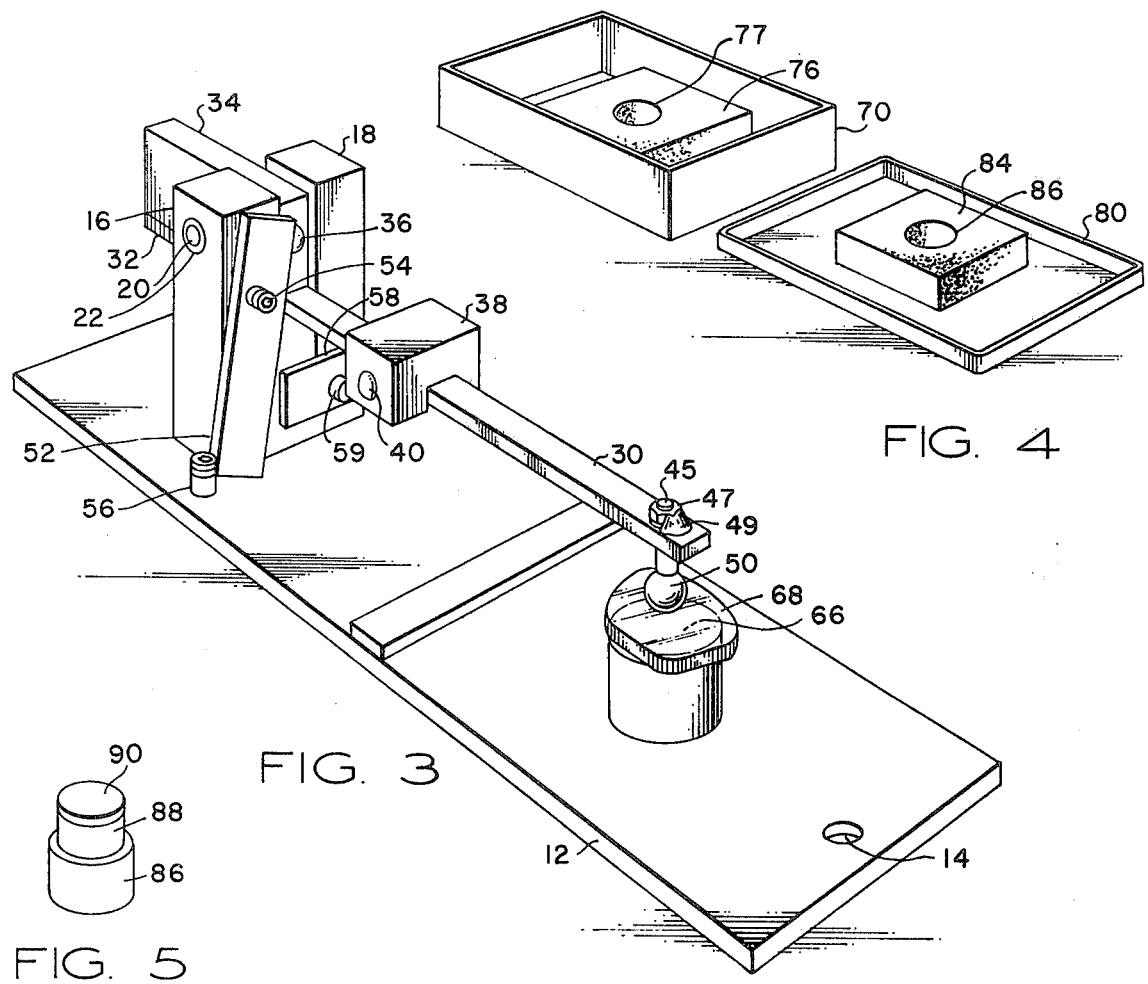
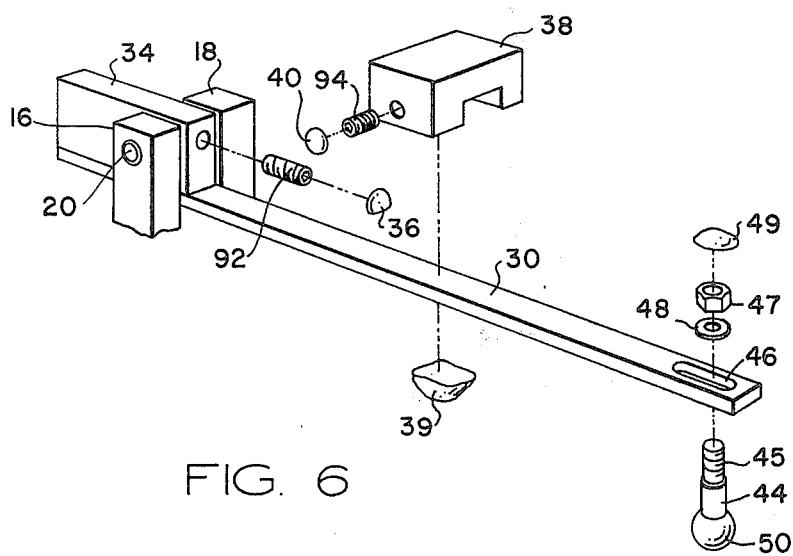

LENS IMPACT HAMMER APPARATUS AND METHODS

BACKGROUND OF THE INVENTION

This invention relates to lens frangibility testing apparatus and more particularly to an impact hammer for testing the strength of eyeglass lenses.

The regulations of the Food and Drug Administration require that eyeglass lenses must be capable of withstanding the impact force generated by a five-eighths inch diameter steel ball weighing approximately 0.58 ounces dropped from a height of 50 inches upon the horizontal upper surface of the lens. The ball must strike within a five-eighths diameter circle at the geometric center of the lens. The ball may be guided but not restricted in its fall by being dropped through a tube extending to within approximately 4 inches of the lens. The total weight of the base plate and its rigidly attached fixtures is required to be not less than 27 pounds.

The conventional type of lens frangibility testing device is a tower-like structure having a long, verticallydisposed tube with a pedestal at the base for supporting a lens. Since the drop-ball apparatus is normally positioned on a table top, the operator must mount a ladder or some type of platform to place the ball at the top of the tube. Thus, either two persons are required to operate the apparatus or one operator quickly becomes fatigued. Danger of injury from falling presents an additional problem. Alternately, some embodiments utilize a raising device to convey the ball to the top of the device. The apparatus required for this approach is relatively complicated and involves many moving parts, thus increasing maintenance requirements. In either case, precision is a problem since the tube must be larger than the diameter of the ball and cannot extend down to the lens. Thus, the ball may strike at different points on the lens near the center rather than at the exact center, resulting in a considerable degree of inaccuracy and error.

SUMMARY OF THE INVENTION

The present invention concerns a device for impacting an eyeglass lens in the exact center of the lens with a force equivalent to conventional drop-ball apparatus. One person can easily and rapidly operate the device from a sitting position. The device has few moving parts and is operated manually and by the force of gravity.

The lens impact apparatus includes support means mounted on a base member for positioning the lens for impact. Pivot means carrying an impacting means are connected to the base at a spaced distance from the support means. The pivot means are pivotally mounted to the base member to direct the impact means through an arc to strike the lens. Catch means associated with the base member hold the pivot means away from the lens and selectively release the pivot means to impact the lens.

More specifically, hammer apparatus for impacting a lens includes a base support plate with a support pedestal mounted thereon for holding the lens. Bearing means are mounted on the plate a predetermined distance from the pedestal and a hammer arm is pivotally connected to the bearing means for movement from a cocked position to an impact position. An impact member is mounted near the end of the hammer for striking the lens as the hammer arm pivots to the impact position. A catch piece is pivotally connected to the bearing means to hold the hammer in the cocked position and to release the hammer to fall to the impact position. A weight means is positioned on the hammer arm in a precise location to provide a predetermined impact force on the lens as the hammer arm falls to the impact position. A removable enclosure encompasses the support pedestal for collecting broken glass.

The invention includes a method of impacting a lens to test the lens frangibility using a pivotally mounted hammer carrying an impact member. The lens is placed on a support member positioned a precise distance from the hammer. The hammer is pivoted away from the support member to a holding position and released to direct the impact member through an arc to strike the lens substantially at the center of the lens.

The invention further comprises a method of manufacturing lens impact apparatus having a hammer pivotally mounted to strike the lens by pivoting through a gravity-induced arc. The hammer is aligned to strike the lens substantially at the center of the lens. The impact force of the hammer at the end of the arc is measured, and a weight on the hammer is adjusted to provide a predetermined impact force at the end of the arc.

As is obvious from the foregoing summary, the invention provides a lens impact apparatus which can be operated simply and quickly with great accuracy. The apparatus can be easily mounted on a work bench and operated by one person in a seated position. The hammer may be raised and released with one hand while the other hand is used to exchange lenses positioned on the pedestal between impact strokes. Using the apparatus of the present invention, the impact testing time has been found to be reduced by as much as 75%, and one operator is able to process as many as three hundred pairs of lenses an hour.

The present invention has also been found to be extremely accurate since the hammer arm guides the impact ball to the same precise point with each impact stroke. Thus, once the device is properly aligned and assuming that each lens is positioned properly on the support pedestal, the impact ball strikes exactly the same point on the lens each time.

The preferred embodiment of the impact device includes no strings or motors and a minimum of moving parts. The hammer arm is manually moved to the ready position and is driven against the lens by the acceleration of gravity. Thus, a minimum of maintenance is needed to insure long and satisfactory operation of the device. A removable enclosure encompassing the pedestal collects broken glass for efficient disposal and protects the operator from flying splinters. These and other advantages may be seen from the following detailed description of the drawings.

DESCRIPTION OF THE DRAWINGS

A more complete understanding of the invention may be had by referring to the following detailed description taken in conjunction with the drawings wherein:

FIG. 3 is a front perspective view of the lens impact hammer apparatus of FIG. 1 with the hammer arm in impact position and the pedestal enclosed removed;

FIG. 4 is a perspective view of the enclosure box of the present invention with the lid off;

FIG. 5 is a perspective view of an alternate lens support pedestal of the present invention; and FIG. 6 is a partial exploded view of the lens impact hammer apparatus of FIG. 1 showing the alignment process of the hammer arm and impact ball.

Referring now to FIGS. 1 and 2, a lens impact hammer system 10 embodying the present invention is shown. A rectangular base plate 12 includes apertures 13 and 14 at either end for mounting to a work bench or other heavy base. Two support members 16 and 18 are mounted in a parallel upright position on base plate 12. A shaft 20 extends transversely between support members 16 and 18. Shaft 20 is journaled into bearings 22 and 24 located in the upper ends of support members 16 and 18, respectively.

Figure 1:
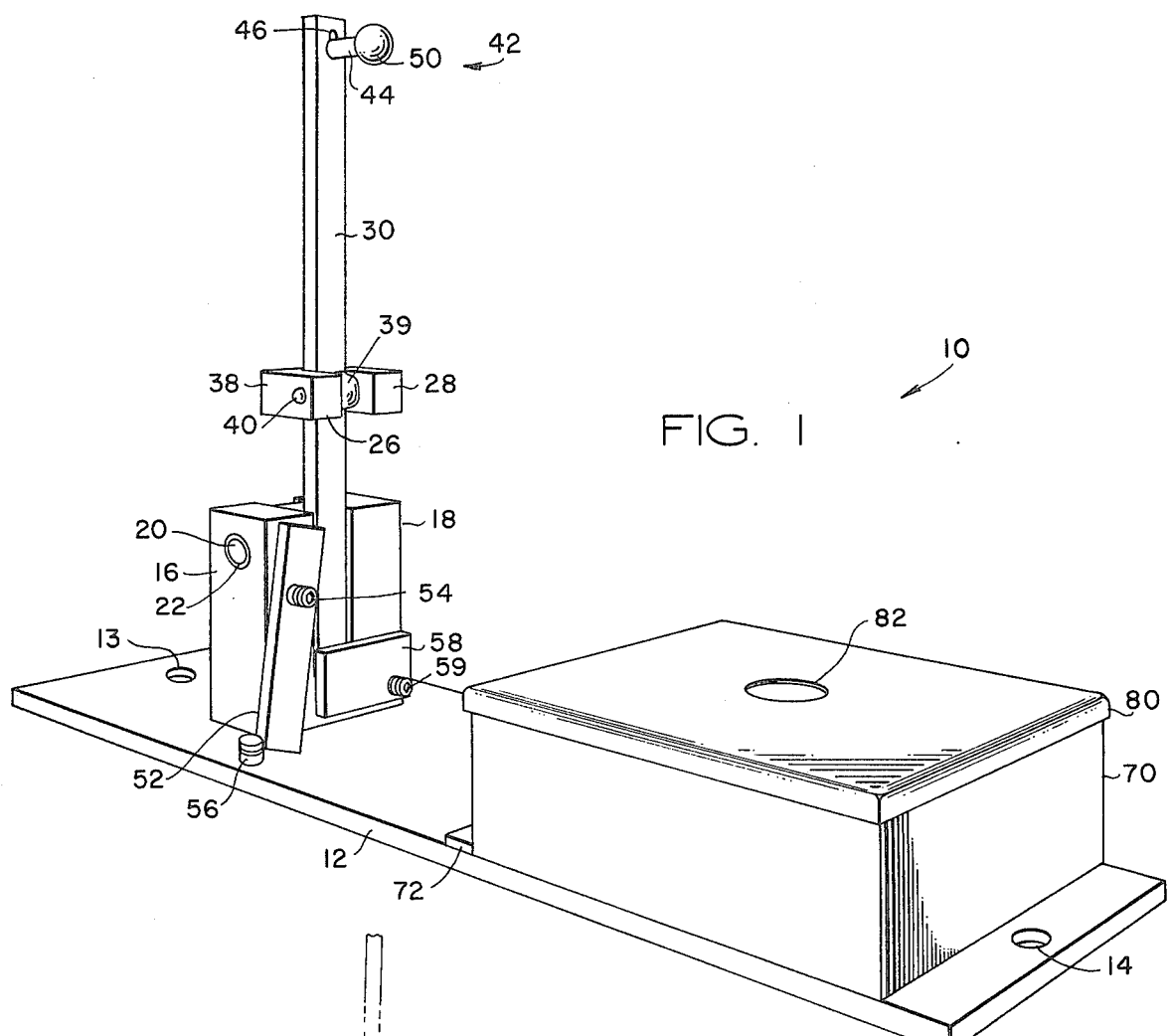
FIG. 1 is a front persepective view of the lens impact hammer apparatus of the present invention.
Figure 2:
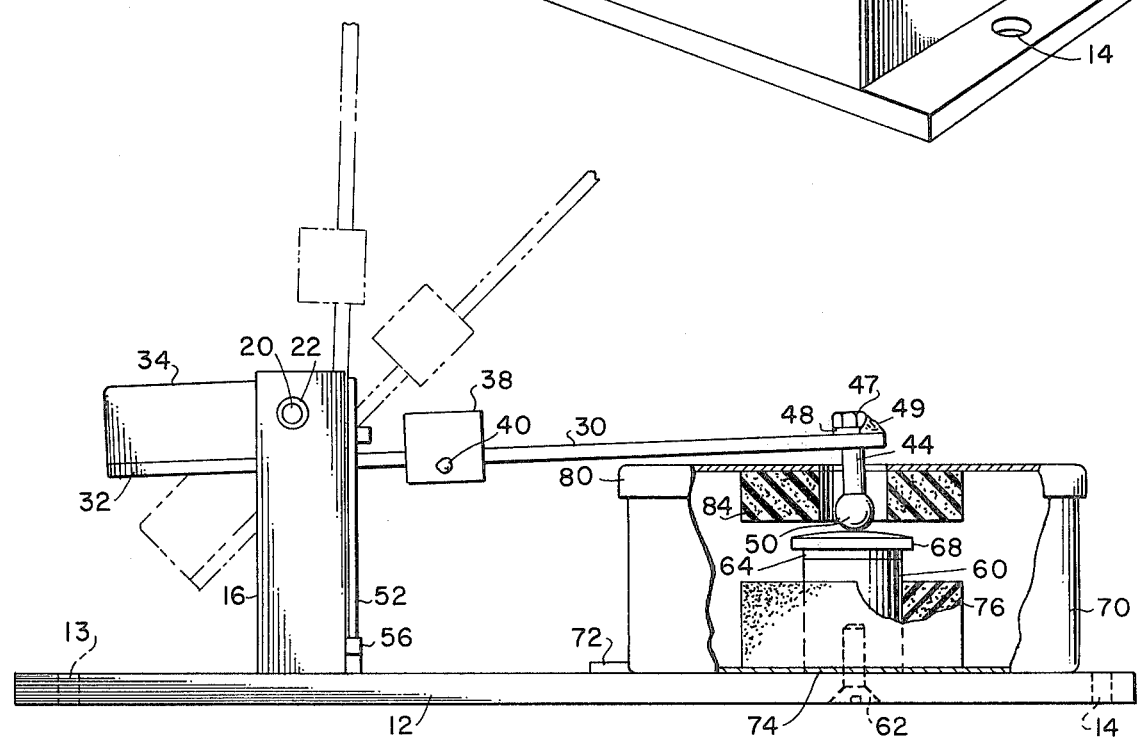
FIG. 2 is a partially cut-away side view of the lens impact hammer apparatus of FIG. 1 with the hammer arm in impact position.

An elongated rectangular hammer arm 30 is mounted to shaft 20 to pivot between support members 16 and 18 between a raised vertical position, shown in FIG. 1, and a lowered horizontal position, shown in FIG. 2. Hammer arm 30 includes a cantilevered portion 32 extending rearwardly from support members 16 and 18 and having a counterweight 34 attached to the top of said cantilevered portion 32. Shaft 20 extends through an aperture in counterweight 34 to secure hammer arm 30. A set screw 92 is inset into the front end of counterweight 34 (FIG. 6) to fit the position of the counterweight with respect to shaft 20. An epoxy portion 36 covers set screw 92 to prevent tampering.

A U-shaped weight 38 straddles hammer arm 30 at a predetermined position and is fastened by a set screw 94 in aperture 95 (FIG. 6). An epoxy portion 40 covers the set screw 94 and another epoxy portion 39 extends between the two legs 26 and 28 in contact with the underside of hammer arm 30.

Near the end of hammer arm 30 opposite the cantilevered portion 32, an impact member 42 is attached. Impact member 42 includes a tubular shaft 44 having a threaded end 45 inserted in a slot 46 in hammer arm 30 and attached by a nut 47 and a washer 48. An impact ball 50 is welded to shaft 44 to extend rigidly below the end of hammer arm 30 for impacting a lens.

A rectangular catch member 52 is pivotally attached to the forward face of support member 16 by a bearing screw 54. Screw 54 is mounted above the midway point of catch member 52 and off center from its longitudinal axis. Member 52 thus tends to pivot to block hammer arm 30 in the vertical position shown in FIG. 1. A vertically extending stop post 56 is attached to base plate 12 to abut the bottom of catch member 52 after the member pivots far enough to block arm 30.

A rectangular blocking piece 58 is rigidly attached to the front of support member 18 by screw 59 to extend between support members 16 and 18 and abut the cantilevered portion 32 when hammer arm 30 is in the vertical position shown in FIG. 1.

As shown in FIG. 2, a support pedestal 60 is mounted on base plate 12 by an inset screw 62. Pedestal 60 is preferably a solid cylindrical metal post mounted along the longitudinal axis of base plate 12 at a precise distance from support members 16 and 18 so that impact ball 50 will strike in the center of the pedestal. A hard, round disc 64, having a diameter substantially the same as that of the pedestal 60, is mounted concentrically on top of pedestal 60. Disc 64 has a flat top surface 66 for supporting a lens 68 as shown in FIG. 3.

A rectangular metal box 70 is positioned on base plate 12 to encompass pedestal 60 and abut a cross member 72 anchored to base plate 12. Box 70 includes an aperture 74 in the center of the bottom of the box through which support pedestal 60 extends. Metal box 60 may be removed from base plate 12 by simply lifting the box upward until aperture 74 is free of pedestal 60, as shown in FIG. 4. A rectangular cushion 76 is attached to the center part of the bottom of box 70 and has a cylindrical aperture 78 through its center to tightly encompass pedestal 60. A rectangular lid 80 is provided with dimensions slightly larger than those of metal box 70 so that the lid will fit snugly over the sides of the box. An aperture 82 is provided in the center of lid 80 having a diameter greater than that of impact ball 50 so that ball 50 may enter through aperture 82 as hammer arm 30 drops downward. A cushion 84, similar to that of cushion 76, is attached to the underside of lid 80 and includes a cylindrical aperture 86 therethrough having a diameter identical to that of aperture 78.

In a preferred embodiment, the device of the present invention is made of lightweight metal, such as aluminum, except for certain parts which require heavier material. The base 12, impact ball 50, weight 38 and pedestal 60 are preferably made of solid steel. Other parts such as the catch member 52 and stop piece 56 may also be made of steel if desired. The circular disc 64 on top of pedestal 60 is preferably of neoprene or some other type of hard elastomeric material. Cushions 76 and 84 are preferably of lightweight styrofoam.

In a preferred embodiment, hammer arm 30 is approximately 8 inches long and cantilevered portion 32 extends 2-½ inches behind the pivot point. The counterweight 34 weighs approximately 2,3 ounces and the impact ball 50 is five-eighths inch in diameter, weighing approximately 0.58 ounces, as required by FDA regulations. Support pedestal 60 is approximately 1⅝ inches high and 1¼ inches in diameter with a 1/8 inch thick disc 64 mounted on top.

In operation, lens hammer impact device 10 is normally operated by one person, preferably seated. Box 70 is positioned on base plate 12 encompassing pedestal 60 with lid 80 removed. With one hand, the operator pushes downward on counterweight 34, causing arm 30 to raise. Catch member 52 rides along the adjacent edge of arm 30 and gradually rotates to a vertical position as the arm is raised. When the arm reaches a substantially vertical position, catch member 52 drops in front of the arm blocking downward movement. Blocking piece 58 limits pivoting of hammer arm 30 in a backward direction beyond the vertical position. At this point, hammer arm 30 is in a holding position with the arm resting against catch member 52, slightly forward a few degrees from a truly vertical position.

With the other hand, the operator places a lens to be impacted on support pedestal 60 so that the lens is centered with the convex surface facing upward. The center of the lens is positioned as closely as possible to the center of the pedestal.

The operator now releases catch member 52 from in front of hammer arm 30 by pushing the lower base of member 52 in a counterclockwise direction. Hammer arm 30 falls forward under the force of gravity, directing impact ball 50 through an arc which ends at the surface of lens 68. Weight 38 has been previously adjusted to the precise portion on arm 30 to impart the required impact force to lens 68. If lens 68 has been properly positioned on pedestal 60, impact ball 50 will strike in the exact center of the lens on each impacting stroke with the required force.

The operator raises hammer arm 30 to a vertical position with one hand and with the other hand removes lens 68 and places a new lens on pedestal 60. The same impacting operation is repeated as long as necessary to test the lenses on hand.

Should a lens break, the pieces will fall onto cushion 76 and into the bottom of box 70. Hammer arm 30 is then cocked and box 70 is slipped off pedestal 60 and emptied. Cushion 76 provides a tight fit around pedestal 60 to prevent small glass pieces from falling through aperture 74. The use of lid 80 is optional, since the broken glass pieces normally do not fly out of box 70. If desired, lid 80 is placed over box 70 after lens 68 is positioned on pedestal 60. Cushion 84 rests just above lens 68 on the underside of lid 80. When arm 30 is released, impact ball 50 penetrates aperture 82 to strike lens 68. Shaft 44 is long enough to allow ball 50 to impact lens 68 without arm 30 striking the top of lid 80 or the top of box 70. Preferably shaft 44 is about 1½ inches long.

As shown in FIG. 5, an alternate support pedestal 86 has a second upper portion 88 with a smaller diameter than that of support pedestal 60. The diameter of upper portion 88 is preferably ⅞ inches to accommodate small lenses. A ½ inch thick neoprene disc 90 having the same diameter is mounted on upper portion 88.

With reference to FIG. 6, the method of aligning certain elements of the present invention is shown. After the basic elements of the impact device 10 have been assembled on base plate 12, hammer arm 30 and impact ball 50 are adjusted for proper alignment. Hammer arm 30 and counterweight 34 are shifted traversely along shaft 20 until the end of hammer arm 30 falls directly in the center of support pedestal 60. Set screw 92 is tightened into aperture 93 to fasten hammer arm 30 rigidly to shaft 20. The threaded end of shaft 44 is inserted through slot 46 on the end of hammer arm 30 and loosely fastened by nut 47 and washer 48. Arm 30 is placed in a horizontal position and shaft 44 is moved in slot 46 until ball 50 is in the exact center of pedestal 60. It may be necessary at this point to loosen set screw 92 and readjust the location of counterweight 34 relative to shaft 20. When ball 50 is correctly positioned, nut 48 is tightened firmly to secure the shaft in slot 46.

Weight 38 is placed on hammer arm 30 in an approximate position determined from previous alignments. Set screw 94 is tightened in aperture 95 against the side of hammer arm 30 to hold the weight 38 in place. Cut portions of unmixed ribbon epoxy are positioned over set screws 92 and 94, over nut 47, and between legs 26 and 28. The weights of epoxy portions 36, 40, 49 and 39 are thereby included in the adjustment process to enhance accuracy. An impact testing device is positioned in place of pedestal 60 on base plate 12. The testing device used may be any impact gauge capable of measuring fractional foot pounds and having a height identical to that of the support pedestal 60.

Hammer arm 30 is raised to a vertical position and released to impact against the testing device which registers the striking force. The required force created by a five-eighths inch steel ball weighing 0.58 ounces and falling through 50 vertical inches is 0.152 foot pounds. If the impact force registered by the testing device is shown to be less than the required amount, set screw 94 is loosened and weight 38 is moved forward toward the outer end of hammer arm 30. Conversely, if the testing device registers an impact force in excess of the required amount, set screw 94 is loosened and weight 38 is moved backward toward the pivot point of hammer arm 30. When the testing device registers exactly 0.152 foot pounds, set screw 94 is tightened firmly into place. The unmixed epoxy ribbon portions are then individually mixed and epoxy portions 36 and 40 are applied to set screws 92 and 94, respectively. Epoxy portion 49 is applied to nut 47 to hold it firmly in place. Epoxy portion 39 is placed on the underside of hammer arm 30 in contact with both legs of the U-shaped weight 38. Epoxy portions 36, 39, 40 and 49 serve to prevent further adjustment or tampering with the hammer arm 30, impact ball 50 or weight 38 to preserve the precision of the impact device.

Hammer arm 30 is cocked into the vertical position and the impact testing gauge is removed. Support pedestal 60 is placed back in position on base plate 12 and the position of impact ball 50 with relation to the center of support pedestal 60 is again checked to insure accuracy. The impact device is then appropriately packed and crated with the necessary padding to insure that the precise settings will not be disturbed during shipment.

When the impact device is set up for operation, base plate 12 is mounted on a base weighing at least 27 pounds in order to comply with government regulations. A heavy steel base may be connected directly to base plate 12. Alternately, the base plate may be mounted on a heavy solid work bench. If the impact device is attached to a heavy piece of wood, care should be taken to attach metal between the base plate and the wood in order to comply with governmental requirements.

It is obvious that certain modifications may be made to the impact device as described herein without departing from the scope of the invention. For example, larger or smaller impact balls may be used for special lens requirements. A one inch diameter steel ball may replace the standard impact ball for testing industrial safety lenses. Likewise, different sized or differently shaped pedestals may be employed for special situations. Precise coil springs or other resilient elements may be connected to the hammer arm to supplement the force of gravity acting on the arm. Likewise, a number of different types of catches or triggers may be employed to hold and release the hammer arm. Moreover, the catch member may be entirely eliminated so that the hammer arm is held manually in the vertical position until release is desired.

Although a particular embodiment of the invention has been illustrated in the accompanying drawings and described in the foregoing description, it will be understood that the invention is not limited to the embodiment disclosed but is capable of rearrangement, modification and substitution without departing from the spirit of the invention.

What is claimed is:

1. Lens impact apparatus for testing the frangibility of a lens comprising:
   a base member;
   means on said base member for supporting said lens in position for impact;
   means for impacting said lens positioned on said support means;
   pivot means including a rigid arm member attached to said base member at a position spaced from said support means for directing said impact means through an arc from a first position with said impact means spaced from said lens on said support means to a second position with said impact means in contact with said lens, said arm member having a weight member movable along said arm member for varying the force that said weight member exerts against said lens on said support member as said arm member reaches said second position; and catch means associated with said base member for holding said pivot means in said first position and for selectively releasing said pivot means to move to said second position.

2. The lens impact apparatus of Claim 1 wherein said arm member is mounted for positioning substantially vertically with said impact means in said first position and for falling by the force of gravity to a horizontal position with said impact means in said second position.

3. The lens impact apparatus of Claim 1 wherein said weight member further comprises a weight slidable along said arm member and having means for abutting said arm member to hold said weight in a position so that said weight member will exert said predetermined force against said lens on said support member as said arm member reaches said second position.

4. The lens impact apparatus of Claim 1 wherein said arm member is mounted with a cantilevered portion extending along the longitudinal axis of said arm member, and further comprising a counterweight mounted on said cantilevered portion for partially offsetting the weight of said arm member.

5. The lens impact apparatus of claim 4 and further comprising stop means for abutting said cantilevered portion to limit backward movement of said arm member through said arc to said first position.

6. The lens impact apparatus of claim 1 wherein said impact means comprises a round ball mounted on the end of said arm member to impact said lens substantially in the center of said lens.

7. The lens impact apparatus of Claim 1 wherein said support means comprises a cylindrical pedestal mounted upright on said base member and positioned on said base member to support said lens for striking by said impact means.

8. The lens impact apparatus of Claim 1 wherein said catch means comprises a pivot piece mounted in association with said base member to pivot between a blocking position holding said arm member in said first position, and a release position allowing said arm member to move to said second position.

9. Hammer apparatus for impacting a lens comprising:
a base support plate;
a support pedestal mounted on said plate for holding said lens;
bearing means mounted on said plate a predetermined distance from said pedestal;
a hammer arm pivotally connected to said bearing means for movement from a cocked position to an impact position;
an impact member mounted near the end of said hammer arm for striking said lens as said hammer arm pivots to said impact position; and
an adjustable weight on said arm movable for positioning along said arm whereby the force with which said impact member strikes said lens may be varied in accordance with predetermined criteria.

10. The hammer apparatus of Claim 9 and further comprising a catch piece connected to said bearing means to pivot by gravity and hold said hammer arm in said cocked position and manually releasable to allow said hammer arm to fall toward said impact position.

11. The hammer apparatus of Claim 9 and further comprising a weight means adjustably movable on said hammer arm for varying the force of said impact member on said lens as said hammer arm moves to said impact position.

12. The hammer apparatus of claim 9 and further comprising a removable enclosure on said base support plate encompassing said support pedestal and having an aperture in the top of said enclosure above said pedestal for admitting said impact member as said hammer arm moves to said impact position.

13. The hammer apparatus of claim 12 wherein said enclosure comprises a removable top member having said aperture therein, and a corresponding bottom member having a second aperture with said pedestal protruding therethrough, said bottom member thereby collecting broken pieces for said impacted lens.

14. The method of manufacturing lens impact apparatus having a hammer pivotally mounted to strike said lens with a predetermined force by pivoting through an arc, comprising:
aligning said hammer to strike said lens substantially at the center of said lens;
positioning a weight on the arm of said hammer at a position to provide approximately said predetermined force by said hammer;
determining the impact force of said hammer at the end of said arc with the weight in said position; and
moving the position of said weight along the arm of said hammer and repeating said determining step until the hammer strikes the lens with said predetermined impact force at the end of said arc.

15. The method of Claim 14 wherein said aligning step comprises adjusting a lever arm on said hammer in a direction traverse to the longitudinal axis of the lever arm, and adjusting an impact ball on the end of said lever arm in a direction parallel to the longitudinal axis of the lever arm.

16. The method of Claim 15 and further comprising the step of fastening said lever arm and said impact ball in position to maintain said alignment.

17. The method of claim 14 and further comprising the step of fastening said weight in the moved position to maintain said predetermined impact force.

18. Lens impact apparatus for testing the frangibility of a lens comprising:
a base member;
means on said base member for supporting said lens in a substantially horizontal position; and
hammer means mounted on said base member at a position spaced apart from said supporting means for striking said lens, said hammer means including a lever arm pivotal between a substantially vertical position and a substantially horizontal position, and impact means on said lever arm for impacting said lens, said lever arm being mounted for manual rotation to said vertical position and for manual release to fall by gravity to said horizontal position, said impacting means being mounted to said lever arm for traversing a substantially 90 degree arc as said lever arm moves between said first and second positions, said impacting means including a ball attached to the end of said lever arm, said ball being adjustably movable along the longitudinal axis of said lever arm to vary the point of impact of said ball on said lens.

* * * * *